United States Patent [19]

Roelofs et al.

[11] Patent Number: 5,296,220
[45] Date of Patent: Mar. 22, 1994

[54] COCKROACH ATTRACTANT

[76] Inventors: Wendell L. Roelofs, 4 Crescence Dr., Geneva, N.Y. 14456; Coby Schal, 246 Edinburg Rd., Mercerville, N.J. 08619; Francis X. Webster, 302 Hurlburt Rd., Syracuse, N.Y. 13224; Ralph E. Charlton, 780 Tabor Valley Rd., Manhattan, Kans. 66502; Aijun Zhang, 15 Reed Rd., Apt. 125, Geneva, N.Y. 14456

[21] Appl. No.: 986,054
[22] Filed: Dec. 7, 1992
[51] Int. Cl.$^5$ .............. C07D 309/32; C07D 309/18; A01N 25/00; A01N 25/24
[52] U.S. Cl. .............................. 424/84; 549/292
[58] Field of Search .......................... 549/292; 424/84

[56] References Cited

U.S. PATENT DOCUMENTS

| | | | |
|---|---|---|---|
| 3,111,529 | 11/1963 | Lohaus et al. | 549/294 |
| 3,151,126 | 9/1964 | Lohaus et al. | 549/294 |
| 3,318,912 | 5/1967 | Scott | 549/292 |
| 3,743,718 | 7/1973 | Comeau et al. | 424/84 |
| 3,818,047 | 6/1974 | Henrrick | 549/294 |
| 3,845,108 | 10/1974 | Roelofs et al. | 560/261 |
| 3,873,586 | 3/1975 | Henrick | 554/213 |
| 4,255,444 | 3/1981 | Oka et al. | 549/292 |
| 4,339,388 | 7/1982 | Still | 549/332 |
| 4,568,757 | 2/1986 | Carroll et al. | 549/294 |
| 4,844,892 | 7/1989 | Laurence et al. | 424/84 |
| 5,011,944 | 4/1991 | Kvits et al. | 549/292 |
| 5,084,392 | 1/1992 | Miyazawa et al. | 549/292 |

OTHER PUBLICATIONS

A. Belanger et al., 15 *J. Chem. Soc., Chem. Commun.* 863-4 CA 77(19) 126361b.
R. T. Carde et al., "Attraction of Redbanded Leafroller Moths", *Argyotaenia velutinana*, [1] To Blends of (Z)- and (E)-11-Tridecenyl Acetates, 3 *J. Chem. Ecol.* 143-149 (1977).
C. Schal et al., "Integrated Suppression of Synanthropic Cockroaches", 35 *Annu. Rev. Entomol.* 521-51 (1990).
R. J. Steltenkamp et al., "Alkyl and Aryl Neoalkanamides: Highly Effective Insect Repellents", 29 *J. Med. Entomol.* 141-149 (1992).
T. A. Granovsky, "Effect of Exterior Surface Texture on Cockroach Jar Trap Efficacy", 12 *Environmental Entomology* 744-7 (Jun. 1983).
Y. S. Chow et al., "Attraction Responses of the American Cockroach to Synthetic Periplanone-B", 7 *Journal of Chemical Ecology* 265-72 (1981).

(List continued on next page.)

*Primary Examiner*—C. Warren Ivy
*Assistant Examiner*—A. Owens
*Attorney, Agent, or Firm*—Nixon, Hargrave, Devans & Doyle

[57] ABSTRACT

Compounds useful as cockroach attractants, the synthesis of the compounds, and methods of controlling cockroach populations with the compounds are disclosed. The compounds are pyrans having the formula:

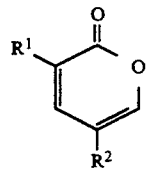

wherein:
$R^1$ is a methyl, ethyl, propyl, or methoxy group and
$R^2$ is a branched alkyl side chain having from 7 to 11 carbons. Preferably, $R^2$ is a 2,4-dimethyl-substituted alkyl group. Most preferably $R^1$ is methyl and $R^2$ is 2,4-dimethylheptanyl. The pyrans can be used as an attractant in cockroach traps comprising, in addition to a pyran according to Formula (I) above, a support and a cockroach restraint. Alternatively, the pyran of the present invention can be combined with a biocontrol agent or an insecticide to form a cockroach control composition.

15 Claims, 4 Drawing Sheets

OTHER PUBLICATIONS

W. J. Bell et al., "Attraction of American Cockroaches (Orthoptera: Blattidae) to Traps Containing Periplanone B and to Insecticide-Periplanone B Mixtures", 13 *Environ, Entomol.* 448-450 (1984).

M. K. Rust et al., "Increasing Blatticidal Efficacy with Aggregation Pheromone", 70 *Journal of Economic Entomology* 693-696 (1977).

A. V. Barak et al, "Using Attractant Traps to Help Detect and Control Cockroaches", *Pest Control* 14-20 (Oct. 1977).

A. Belanger et al., "Reactions of Ketene Acetals. III. A New Synthesis of α-Pyrones. II", 53 *Can. J. Chem.* 195-200 (1975).

COCKROACH ATTRACTANT

FIELD OF INVENTION

This invention relates to attractants for cockroaches.

BACKGROUND OF THE INVENTION

Cockroaches have long been recognized as pests of economic and aesthetic concern. They have become increasingly important in public health and veterinary medicine. For example, it is well known that cockroaches regularly move between sewers and human food materials. As a result, cockroaches acquire, carry, and transfer pathogens either mechanically or in their digestive system. This problem is especially evident in public housing, where cockroach populations are large and problems such as salmonellosis are particularly prevalent. Cockroaches also serve as intermediate hosts for the spiny-headed worms that infect the small intestines of vertebrates. Hypersensitivity to cockroaches is particularly common among inner-city residents and workers in entomological laboratories where both intensity and duration of exposure are high. Therefore, the need for effective suppression of cockroach populations to alleviate health-related problems (as well as aesthetic concerns) is self-evident.

The need to suppress cockroach populations has resulted in the use of large amounts of pesticides in urban environments. However, use of broad spectrum toxins for insect control is a serious environmental risk. In addition, broad spectrum toxins foster insecticide resistance and make subsequent insect control more difficult. Accordingly, there is a continuing need for the development of safe, effective, and environmentally compatible insect control techniques.

In recent years, compounds known as pheromones have been recognized as useful components of a successful pest control program. A pheromone is generally defined as a chemical substance secreted by living organisms, including insects, to convey information or produce a specific response in other individuals of the same species. Sex pheromones typically take the form of a complex, volatile blend of compounds which is, for example, excreted during the mating cycle. As such, sex pheromones often serve as "attractants"; that is, the pheromone attracts insects of the same species to the location of the pheromone emission.

There are several pheromones used by cockroaches, including those used at a distance (volatile), at close range (mostly male tergal secretions), and by contact only (cuticular components). However, only long distance pheromones are practically useful in pest control programs. To date, only three structures having attractant activity relative to test cockroaches have been characterized. These attractants are generally known as periplanone B, periplanone A, and periplanone J, respectively. The pheromonal activity of these compounds is, however, restricted to cockroaches of the genera Periplaneta and Blatta.

Attractants for many other cockroaches have not been developed. One cockroach species for which no structure having pheromonal activity has been synthesized is *Supella longipalpa*, also known as the "brown-banded cockroach." The brown-banded cockroach, however, poses an ever-increasing pest control problem. First observed in the continental United States in 1903, brown-banded cockroaches have been collected throughout the United States in recent years and have become a major pest in many regions of the southern United States. In the Northeast, brown-banded cockroach infestations are most common in areas where pesticide usage is restricted, e.g., schools, hospitals, nursing homes. They are also an important pest in tropical and subtropical regions. Therefore, an object of this invention is to provide chemical compounds that exhibit sex attractant activity relative to the brown-banded cockroach.

SUMMARY OF THE INVENTION

The present invention relates to attractants for cockroaches, as well as the synthesis and use of these compounds. In accordance with the present invention, we have unexpectedly discovered that pyrans having a specified formula are effective attractants for cockroaches, primarily male cockroaches, including the brown-banded cockroach. Pyrans useful as cockroach attractants have the following formula:

wherein $R^1$ is an H, methyl, ethyl, propyl, or methoxy group and $R^2$ is a branched alkyl side chain having from 7 to 11 carbons. Preferably, $R^2$ is a 2,4-dimethyl-substituted alkyl group. Most preferably, $R^1$ is methyl and $R^2$ is 2,4-dimethylheptanyl.

The pyrans of the present invention are made by a method including the steps of: forming an alcohol by Grignard alkylation of a first epoxide (the epoxide having between 2 to 7 carbons), substituting the hydroxy group of the alcohol with a halide to form an alkyl halide, Grignard coupling the alkyl halide with methallyl chloride to form an olefin, epoxidizing the olefin to form a second epoxide, forming an allylic alcohol by $\beta$-elimination of the second epoxide, performing an orthoester Claisen rearrangement of the allylic alcohol to form an ester, hydrolyzing the ester to form a first carboxylic acid having an olefin moiety, oxidatively cleaving the olefin moiety to form a ketone, forming an enol ether by Wittig olefination of the ketone, hydrolyzing the enol ether to form an aldehyde, condensing the aldehyde with a second carboxylic acid to form an enol lactone, and dehydrogenating said enol lactone to form a pyran according to the present invention.

A method and apparatus for trapping cockroaches using the pyrans of the present invention are also disclosed. The method of the present invention includes exposing cockroaches to a trap charged with a suitable amount of an attractant (e.g., between about $1 \times 10^{-4}$ to 100.0 $\mu$g) in the form of a pyran according to the formula described above. Cockroach control apparatus according to the present invention include a support, a cockroach restraint, and a cockroach attractant in the form of a pyran according to the formula described above. In an alternative embodiment, the cockroach attractant of the present invention can be combined with a biocontrol agent or an insecticide to form cockroach control compositions. Optionally, such a composition can be placed on a support.

Pyrans according to the present invention are effective, useful cockroach attractants.

DETAILED DESCRIPTION OF THE INVENTION

The present invention relates to compounds useful as attractants for cockroaches, the synthesis of these compounds, and the use of these compounds in the management of infestations of this pervasive pest. Compounds useful as cockroach attractants are 3,5-disubstituted-2H-pyran-2-ones. More specifically, the inventive compounds are pyrans having the formula:

(I)

wherein:
$R^1$ is an H, methyl, ethyl, propyl, or methoxy group and
$R^2$ is a branched alkyl side chain having from 7 to 11 carbons. Preferably, $R^2$ is a 2,4-dimethyl-substituted alkyl group. Most preferably, $R^1$ is methyl and $R^2$ is 2,4-dimethylheptanyl. The structure of Formula (I) encompasses four stereoisomers formed due to the presence of two chiral centers in the $R^2$ group. An attractant blend can be formed from two or more of the stereoisomers of the compound. Furthermore, the attractant blend can be racemic blend of all four stereoisomers of the compound.

Compounds described by Formula (I) above can be synthesized by first performing a Grignard alkylation on an epoxide to form an alcohol. The epoxide should have between 2 to 7 carbons (e.g., propylene oxide). The next step is halide substitution of the alcohol, preferably with a bromide group, to form an alkyl halide. A Grignard coupling is then performed to couple the alkyl halide with a methallyl halide (e.g., methallyl chloride) to form an olefinic alkyl halide. The olefin moiety is epoxidized to form a second epoxide, from which an allylic alcohol is formed by β-elimination.

The next step in the synthesis of the compounds of the present invention allows modification of the 3- and 5-positions of the pyran. In this step, an orthoester Claisen rearrangement of the alcohol is performed to form an ester. The orthoester Claisen rearrangement is accomplished by utilizing an orthoester (e.g., triethyl orthopropionate) and an allylic alcohol. The substituent on the 3-position of the resulting pyran can be changed by modifying the orthoester. The substituent on the 5-position is dependent on the allylic alcohol used.

Next, the ester is hydrolyzed to form a carboxylic acid having an olefin moiety. A ketone is then formed by oxidative cleavage of the olefin moiety. The next step involves a Wittig olefination to form an enol ether which is then hydrolyzed to yield an aldehyde acid having the following formula:

(II)

wherein:
$R^1$ is an H, methyl, ethyl, propyl, or methoxy group and
$R^2$ is a branched alkyl side chain having from 7 to 11 carbons. Preferably, $R^2$ is a 2,4-dimethyl-substituted alkyl group. Most preferably, $R^1$ is methyl and $R^4$ is 2,4-dimethylheptanyl.

Next, a vacuum distillation is performed to convert the aldehyde acid of Formula (II) to a δ-enol lactone having the following formula:

(III)

wherein:
$R^1$ is an H, methyl, ethyl, propyl, or methoxy group and
$R^2$ is a branched alkyl side chain having from 7 to 11 carbons. Preferably, $R^2$ is a 2,4-dimethyl-substituted alkyl group. Most preferably, $R^1$ is methyl and $R^2$ is 2,4-dimethylheptanyl. In accordance with the present invention, it has been found that enol lactones according to Formula (III) exhibit behavioral activity.

Finally, the δ-enol lactone of Formula (III) is dehydrogenated to form the cockroach pheromone of Formula (I). The synthesis of the novel pyrans of the present invention is described in greater detail in Example 2 below.

The pyran of the present invention is useful as an attractant for cockroaches, especially the brown-banded cockroach. The pyrans of the present invention can be used in any known method or apparatus of trapping or monitoring cockroaches. Generally, the present method of cockroach control includes the step of exposing the insects to a trap charged with a suitable amount of the pyran of Formula (I), e.g., from about $1 \times 10^{-4}$ to 100.0 μg, preferably $1 \times 10^{-3}$ to $1 \times 10^{-2}$ μg. In these amounts, the attractant lures the cockroaches to the trap where they are restrained and/or killed, thus removing the trapped cockroach from the general population.

Cockroach traps according to the present invention can take any known form, and, in addition to the pyran of Formula (I), include a support and a cockroach restraint. Useful methods of restraint include, for example, physical restraint or entrapment of the cockroach.

The support can be formed from any material suitable for supporting the attractant and the restraint. The support can be flexible (e.g., a cotton or canvas-like material) or rigid. Often, the support is in the form of a rigid, inexpensive material such as cardboard.

The cockroach restraint can be an adhesive material which is placed on the support in conjunction with the attractant. Typical adhesive materials are glue or tanglefoot.

The cockroach restraint can also be a mechanical barrier such as a door constructed to allow cockroaches to enter the trap but not exit. Another form of trap utilizing a mechanical restraint is known generally as a "pit-fall" trap. In pit-fall traps, insects are attracted to and fall through an opening into, for example, water or some other container that prevents escape.

Further details regarding the use and construction of cockroach traps using adhesives and/or mechanical barriers are disclosed in: C. Schal and R. L. Hamilton, *Integrated Suppression of Synanthropic Cockroaches*, 35 Annu. Rev. Entomol. 521-551 (1990); Ballard et al., *The Effect of Selected Baits on the Efficacy of a Sticky Trap in the Evaluation of German Cockroach Populations*, 55 J. Kans. Entomol. Soc. 86-90 (1982); Barak et al., *Using Attractant Traps to Help Detect and Control Cockroaches*, 14 Pest Control 14-20 (Oct. 1977); and Bell et al., *Attraction of American Cockroaches (Orthoptera: Blattidae) to Traps Containing Periplanone B and to Insecticide-Periplanone-B Mixtures*, 13 Environmental Entomology 448-450 (April 1984). All of these references are hereby incorporated by reference.

The attractant of the present invention can also be used in conjunction with an insecticide. Because insecticides are generally repellent to cockroaches, the combination of both an attractant such as the pyran of Formula (I) and an insecticide can have enhanced effectiveness over use of an insecticide alone. Useful insecticides include, for example, compounds containing inorganic insecticides (e.g., boric acid, silica gel), organophosphates (e.g., diazinon, chlorpyrifos, propetamphos, acephate), carbamates (e.g., propoxur), pyrethroids (e.g., cypermethrin), sulfluramid, and insect growth regulators. The insecticide can be in the form of, for example, sprays (e.g., emulsifiable concentrates, wettable powders, etc.), aerosols, dusts, baits, granular formulations, laminated slow release formulations, or any other suitable form.

The attractant can be combined with the insecticide and used without a support. Likewise, the attractant can be combined with an insecticide on a support without a restraint (e.g., in a product such as the "Lure n' Kill ™ Killing Station", sold by the Hercon Environmental Co., Emigsville, Pa.). The combination of an insecticide and an attractant can also be used in the traps described above (i.e., with a cockroach restraint).

Further details regarding the combination of attractants and insecticide in sprays or in cockroach traps are disclosed in, for example, M. Rust and A. Reierson, *Increasing Blatticidal Efficacy with Aggregation Pheromone*, 70 Journal of Economic Entomology 693-696 (December 1977); and Bell et al., *Attraction of American Cockroaches (Orthoptera: Blattidae) to Traps Containing Periplanone B and to Insecticide-Periplanone-B Mixtures*, 13 Environmental Entomology 448-450 (April 1984). All of these references are hereby incorporated by reference.

In addition to use in traditional traps, the pyran of the present invention can also be used as an attractant in conjunction with cockroach biocontrol agents. For the purposes of the present invention, a biocontrol agent is defined as any biological enemy (e.g., predator, pathogen, parasite) of the insect pest. Examples of biocontrol agents include pathogenic nematodes, fungi, yeast, bacteria, and viruses. In use, the attractant lures cockroaches to a dissemination station (or to isolated biological agents, if sprayed) where the cockroaches are infected with the biocontrol agent. A dissemination station is a location to which insects are attracted and infected with a biocontrol agent. The cockroaches then return to aggregations and disseminate the agent to the rest of the population. As a result, an entire infestation of cockroaches can be reduced by luring and infecting a few members of the population with the appropriate pathogen.

The present pyran can also be used in concert with repellents to draw cockroaches away from sensitive structures, such as hospitals or restaurants, as disclosed in R. J. Steltenkamp et al., *Aryl and Alkyl Neoalkanamides: Highly Effective Insect Repellents*, 29 Journal of Medical Entomology 141-149 (March 1992).

The present pyran can also be used to disrupt mating within a cockroach population. This is done by exposing a cockroach population to a pyran according to Formula (I) in a quantity sufficient to cover the pheromone emissions by the female cockroaches and thereby prevent potential mates from finding each other, thus disrupting the ability of the cockroaches to mate.

EXAMPLES

Example 1

Isolation of Naturally Occurring Pheromone from Brown-banded Cockroaches

The following example describes the isolation of pheromone from female brown-banded cockroaches for comparative analysis with the compounds of the present invention. Initially, crude hexane extracts were obtained from the tergites of female brown-banded cockroaches. These extracts were purified by silica gel column chromatography. The column was eluted with hexane, three hexane-methylene chloride mixtures (9:1, 4:1, 1:1), ethyl acetate, and, finally, methanol. Next, biological activity was established using a plexiglass two-choice olfactometer assay as described in Liang and Schal, *Effects of pheromone concentration and photoperiod on the behavioral response sequence to sex pheromone in the male brown-banded cockroach, Supella longipalpa*, 3 Journal of Insect Behavior 211-223 (1990). Biological activity resided virtually exclusively in the ethyl acetate fraction of the female extract. Male response to 1/1000th of a female extract was readily detectable.

Active fractions were monitored by recording electroantennograms ("EAGs") according to the procedure described in Schal et al., *Site of pheromone production in female Supella longipalpa (f.) (Dictyoptera: Blattellidae):*

Behavioral, electrophysiological, and morphological evidence, 85 Annals of the Entomological Society of America 605–611 (1992). The active fraction was concentrated and further purified by chromatography on 3% OV-101 non-polar gas liquid chromatography ("GLC") followed by injection on a 30 meter Carbowax TM column (heated at 80° C. for two minutes, temperature then increased 5° C. per minute to 220° C. , where the temperature was held for 20 minutes). Analysis of the purified sample showed a single major peak having a retention time of 24.8. The tergites of approximately 12,000 female brown-banded cockroaches were used to generate approximately 5 μg of material from the active fraction of the naturally occurring pheromone (hereafter "active fraction"). Nuclear magnetic resonance analysis confirmed the presence of a compound in the active fraction having no more than two stereoisomers.

Example 2

Synthesis of 3-methyl-5-(2,4-heptanyl)-2H-pyran-2-one

In this example, the synthesis of 3-methyl-5-(2,4-heptanyl)-2H-pyran-2-one is described in detail with reference to the following reaction sequence:

a. Synthesis of 2-bromopentane (2)

20.0 g of freshly distilled racemic pentan-2-ol (1) was placed in a 100 ml flask fitted with a magnetic stirrer and a dropping funnel. The pentan-2-ol (1) was cooled to −30° C. by immersing the flask in a dry ice-acetone bath and 22.73 g (0.084 mol) of phosphorus tribromide (PBr₃) (purified by distillation at 170° C.) was slowly added with stirring, keeping the temperature of the mixture below 0° C. After adding the PBr₃, the cooling bath was removed. The mixture was stirred until reaching room temperature and allowed to stand overnight. The mixture was then poured into 50 ml of water and extracted with three 100 ml portions of ether. After separation, the ether layers were washed successively with 100 ml of saturated aqueous sodium bicarbonate solution, 100 ml of water, and 100 ml of brine, and then dried over sodium sulfate. The solution was concentrated under reduced pressure and 2-bromopentane (2) was obtained by distillation at 116°–117° C.

b. Synthesis of 4-methylheptan-2-ol (3)

Next, 5.27 g (0.217 mol) of flame-dried magnesium turnings and 25 ml dry tetrahydrofuran ("THF") were placed in a flamed-out, 1000 ml, three-necked round-bottomed flask equipped with a magnetic stirrer. Iodine crystals were also added to the flask. A solution of 28.18 g (0.188 mol) freshly distilled 2-bromopentane (2) in 250 ml dry THF was slowly added to the flask through a dropping funnel under a nitrogen atmosphere with stirring to keep gentle reflux.

The mixture was heated to reflux gently for three hours until most of the magnesium disappeared. The flask was then cooled to −78° C. in a dry ice-acetone bath and 10.3 ml of a 0.1M solution of dilithium tetrachlorocuparate ($Li_2CuCl_4$) in THF was added to the mixture with stirring. After 15 minutes at −78° C., a solution of 8.39 g (0.144 mol) racemic propylene oxide in 50 ml dry THF was added slowly with stirring. The reaction mixture was allowed to warm to room temperature over two hours and stirred overnight. The reaction was quenched with 150 ml of saturated ammonium chloride solution and extracted with three 100 ml portions of ether. The combined extracts were washed with brine, dried over sodium sulfate, and concentrated in vacuo. Distillation at 150°–170° C. yielded 4-methylheptan-2-ol (3) as a colorless liquid. The use of racemic starting materials, as indicated above, results in racemic products throughout this synthesis.

c. Synthesis of 2-bromo-4-methylheptane (4)

17.50 g (0.135 mol) of 4-methylheptan-2-ol (3) was treated with $PBr_3$ (13.48 g, 0.050 mol) as described above in the manufacture of 2-bromopentane (2). The product was purified by distillation at 165°–185° C. to yield 2-bromo-4methylheptane (4).

d. Synthesis of 2,4,6-trimethyl-1-nonene (5)

Magnesium turnings (2.34 g, 96.26 mmol) and 20 ml of dry THF were next added to a flamed-out, 250 ml three-necked flask fitted with a magnetic stirrer, a dropping funnel, and an upright spiral condenser with a nitrogen source. A solution of 2-bromo-4-methylheptane (4) (15.99 g, 83.28 mmol) in 80 ml of dry THF was added dropwise to the flask with vigorous stirring under gentle reflux. Reflux was continued for three hours after completing the addition until most of the magnesium disappeared.

The reaction mixture was then cooled to −78° C. with a dry ice-acetone bath and 4.7 ml of a 0.1M solution of $Li_2CuCl_4$ in THF was added as catalyst. A solution of methallyl chloride (5.8 g, 64.05 mmol) in 15 ml dry THF was added slowly with stirring to the mixture over 15 minutes. The reaction mixture was allowed to warm to room temperature over two hours and stirring was continued for 12 hours. The reaction mixture was quenched with 25 ml of 2N sulfuric acid, followed by 25 ml of water. The ether layer was separated and the water layer was extracted with three 30 ml portions of ether. The combined organic layers were washed with 25 ml of brine, dried over sodium sulfate, and concentrated in vacuo. The residue was purified by vacuum distillation at 44°–50° C. (pressure 1.5 mm Hg) to yield 2,4,6-trimethyl-1-nonene (5) as a colorless oil.

e. Synthesis of 2,4,6-trimethyl-1,2-epoxynonane (6)

m-Chloroperoxybenzoic acid (7.31 g, 60% purity, 25.42 mmol) was added to a stirred solution of 2,4,6-trimethyl-1-nonene (5) (3.56 g, 21.19 mmol) in 70 ml of dry methylene chloride in a 250 ml flask in an ice bath. The chilled reaction mixture was stirred for one hour, and then stirred vigorously overnight at room temperature. The reaction mixture was cooled to 10° C. before filtering out a white slurry, which was washed with cooled methylene chloride. The combined filtrates were washed three times with cooled aqueous carbonate, water, and brine and dried over sodium sulfate. Evaporation of the solvent yielded a crude oil which was distilled at 65°–70° C. and 1.5 mm Hg to yield pure 2,4,6-trimethyl-1,2-epoxynonane (6).

f. Synthesis of 2-methylene-4,6-dimethylnonan-1-ol (7)

An ice-cold solution of diethylamine (3.48 g, 4.9 ml, 47.55 mmol, dried with KBr) in 10 ml of anhydrous ether was prepared. Next, 19.1 ml of a 2.5M solution of n-butyllithium in hexane was added to the diethylamine solution with stirring under a nitrogen atmosphere. After 10 minutes, a solution of 2,4,6-trimethyl-1,2-epoxynonane (6) (3.50 g, 19.0 mmol) in 10 ml of anhydrous ether was added to the reaction mixture and this mixture was refluxed for one hour. Progress of the reaction was checked by withdrawing samples, quenching with water, and analyzing by TLC. Reaction time was determined to ensure total consumption of the epoxide. Upon completion, the reaction mixture was cooled and poured into ice water. The organic layer was separated and the aqueous layer was saturated with solid sodium chloride and extracted with ether. The combined organic layers were washed with 1N hydrochloric acid, saturated sodium hydrogen carbonate solution, water, and brine. the solution was dried over sodium sulfate and solvent was removed in vacuo. Vacuum distillation at 85°–90° C. yielded 2-methylene-4,6-dimethylnonan-1-ol (7).

g. Synthesis of 4-methylene-2,6,8-trimethylundecanoic acid (9)

Next, several drops of propinoic acid were added to a mixture of triethyl propionate (5.1 g, 28.93 mmol) and 2-methylene-4,6-dimethylnonan-1-ol (7) (2.65 g, 14.4 mmol) and this solution was heated. Ethanol produced during the reaction was removed by distillation. After the theoretical amount of ethanol was distilled, the mixture of ethyl 4-methylene-2,6,8-tri-methylundecanoate (8) and excess triethyl propionate was treated with potassium hydroxide (0.97 g, 17.32 mmol), 5 ml of ethanol, and 3 ml of water. The mixture was stirred for three hours at 80° C. in a water bath. The solution was allowed to cool to room temperature and concentrated under reduced pressure. The resulting thick oil was dissolved in 10 ml of aqueous potassium hydroxide and extracted successively with three 20 ml portions of ether. The water layer was acidified with 6N hydrochloric acid to a pH of 1. The solution was saturated with solid sodium chloride, and extracted with three 20 ml portions of methylene chloride. The extracts were dried over anhydrous sodium sulfate and concentrated in vacuo to yield 4-methylene-2,6,8-trimethylundecanoic acid (9).

h. Synthesis of 4-oxo-2,6,8-trimethyl-undecanoic acid (10)

4-Methylene-2,6,8-trimethylundecanoic acid (9) (2.5 g, 10.42 mmol) was dissolved in 20 ml of carbon tetrachloride and 20 ml of acetonitrile in a 250 ml flask fitted with a magnetic stirrer. Sodium periodate (6.68 g, 31.23 mmol) was suspended in the solution with vigorous stirring. A ruthenium chloride ($RuCl_3$) solution was prepared from $RuCl_3.3H_2O$ containing 1.92 g of $RuCl_3$ per ml of $H_2O$. 40 ml (60.1 mg, 0.29 mmol) of the $RuCl_3$ solution was added to the reaction mixture in one portion and vigorously stirred for eight hours. The solution was extracted with three 50 ml portions of methylene chloride. The organic extracts were combined, dried over sodium sulfate, and the solvent was evaporated. The residue, containing highly colored ruthenium species, was dissolved in 50 ml diethyl ether and filtered through Celite ™. The ether was removed under reduced pressure and the resulting crude acid was mixed with 50 ml of 1N sodium hydroxide and extracted successively with three 25 ml portions of ether. The water layer was then acidified with 6N hydrochloric acid to a pH of 1 and e-.tracted with three 50 ml portions of ether. The combined ether solutions were washed with brine, dried over sodium sulfate, and concentrated in vacuo to yield the ketone acid 4-oxo-2,6,8-trimethylundecanoic acid (10).

i. Synthesis of 4-(2,4-dimethylheptanyl)-5-methoxy-2-methyl-4-pentenoic acid (11)

A solution of diisopropylamine (5.40 ml, 38.53 mmol) in 50 ml dry THF at −78° C. was mixed with 15.41 ml (38.53 mmol) of a 2.5M solution of n-butyllithium in hexane with stirring. After 15 minutes, (methoxymethyl)triphenyl-phosphonium chloride (13.87 g, 39.25 mmol, 97% purity) was slowly added. The temperature of the solution was raised to 0° C. and stirred for another 15 minutes. A solution of 4-oxo-2,6,8-trimethylundecanoic acid (10) (1.90 g, 7.85 mmol) in 20 ml of THF was then added to the reaction mixture and this mixture was stirred at room temperature for 11 hours.

The reaction was quenched by addition of 50 ml of saturated aqueous ammonium chloride. The aqueous layer was acidified hydroxide and extracted successively with three 25 ml portions of ether. The water layer was then acidified with 6N hydrochloric acid to a pH of 1 and extracted with three 30 ml portions of ether. The combined ether layers were washed twice with 100 ml of water to remove excess salt, dried over sodium sulfate, and the ether was evaporated under reduced pressure. The residual oil was dissolved in 40 ml of 1N aqueous sodium hydroxide and extracted with three 40 ml portions of ether. The water layer was then acidified with 6N hydrochloric acid to a pH of 1 and extracted with three 30 ml portions of ether. The combined ether layers were washed successively with water and brine, dried over sodium sulfate, and concentrated in vacuo to yield the enol ether 4-(2,4-dimethylheptanyl)-5-methoxy-2-methyl-4-pentenoic acid (11) as a colorless oil.

j. Synthesis of 4-(2,4-dimethylheptanyl)-2-methyl-5oxo-pentanoic acid (12)

To an ice-cold solution of 4-(2,4-dimethylheptanyl)-5-methoxy-2-methyl-4-pentenoic acid (11) (1.85 g, 6.85 mmol) in 95 ml diethyl ether in a 250 ml flask fitted with a magnetic stirrer and a dropping funnel, 25 ml of a 70 volume percent aqueous solution of perchloric acid was added slowly under a nitrogen atmosphere. After the addition was completed, the solution was stirred at room temperature for ten hours. The reaction mixture was poured into ice water, the organic layer separated, and the aqueous layer thoroughly extracted with three 100 ml portions of ether. The combined organic layers were washed with brine, dried over sodium sulfate, and concentrated in vacuo to yield the aldehyde acid 4-(2,4-dimethylheptanyl)-2-methyl-5-oxo-pentanoic acid (12) as a yellow oil.

k. Synthesis of 4-(2,4-dimethylheptanyl)-2-methyl-δ-enol-lactone (13)

4-(2,4-dimethylheptanyl)-2-methyl-5-oxo-pentanoic acid (12) was converted to the corresponding δ-enol lactone 4-(2,4-dimethylheptanyl)-2-methyl-δ-enol-lactone (13) by vacuum distillation at 130°-136° C. and 0.8 mm Hg pressure.

l. Synthesis of 5-(2,4-dimethylheptanyl)-3-methyl-2H-pyran-2-one (14)

A solution of diisopropylamine (148 μl, 1.06 mmol) in 2 ml dry THF at −78° C. was prepared and 42.4 μl (1.06 mmol) of a 2.5M solution of n-butyllithium in hexane was added. After 30 minutes at −78° C., a solution of 4-(2,4-dimethylheptanyl)-2-methyl-δ-enol-lactone (13)(0.21 g, 0.882 mmol) in 0.5 ml dry THF was added dropwise to form an enolate solution which was stirred at −78° C. for one hour under a nitrogen atmosphere. Next, a separate solution of diphenyl diselenide (0.165 g, 0.529 mmol) dissolved in 1 ml of THF was prepared and bromine (27.3 μl, 0.529 mmol) was added dropwise to this solution and the solution was agitated briefly to dissolve any phenylselenyl bromide (PhSeBr₃) that formed. The PhSeBr₃ solution was then added to the enolate solution. After the reaction mixture was brought to 0° C., 0.5 ml water and 0.1 ml acetic acid were added to the mixture followed by 0.5 ml of 30 weight percent hydrogen peroxide. After stirring for one hour at 0° C., the product was isolated by addition of aqueous sodium bicarbonate and extracted with three 100 ml portions of ether. The combined ether layers were washed with brine, dried over anhydrous sodium sulfate, and concentrated in vacuo to yield an oily residue. The product was purified on silica gel (due to the UV sensitivity of the product) using five volume percent ethyl acetate in hexane as an eluent to yield 5-(2,4-dimethylheptanyl)-3-methyl-2H-pyran-2-one (14).

Example 3

Figure 1:
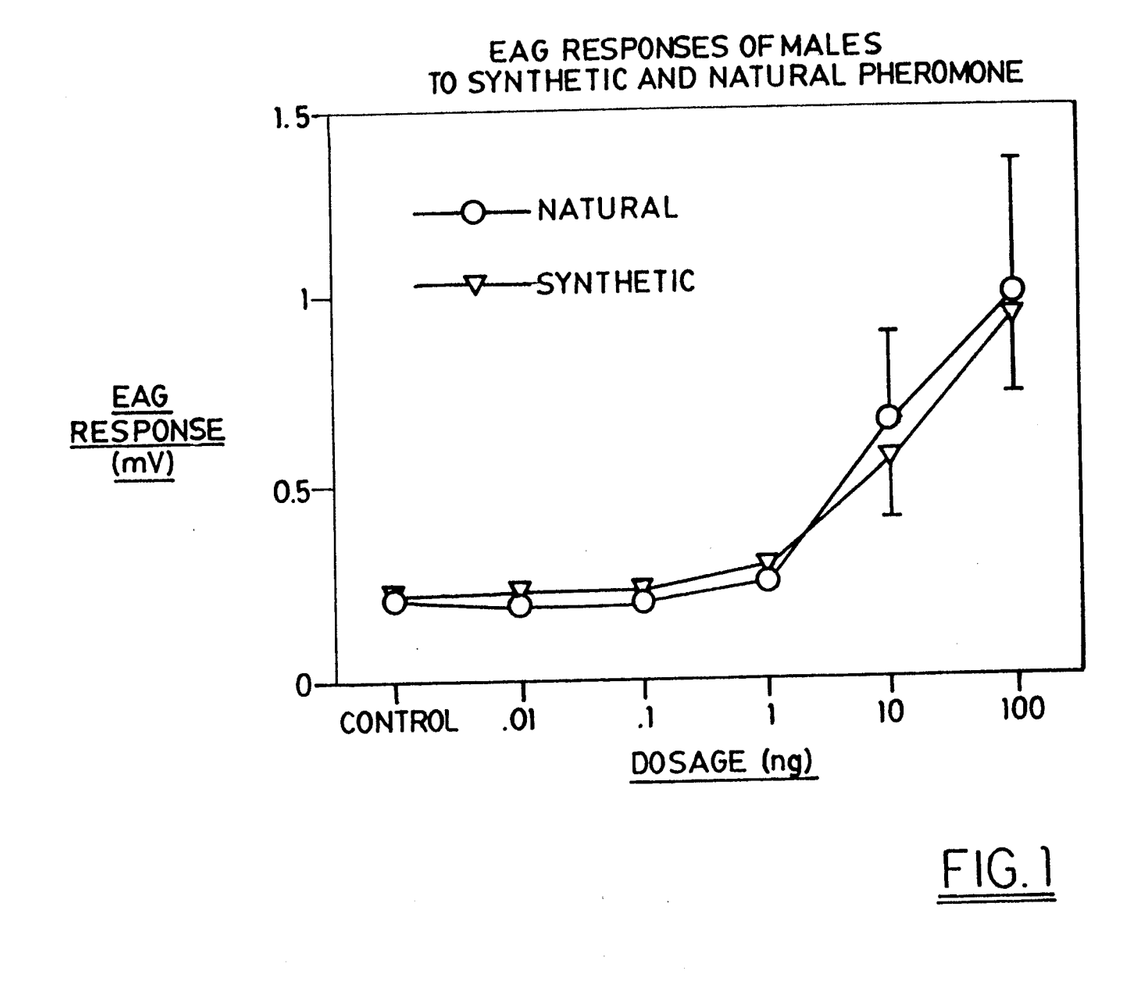
FIG. 1 is a graph illustrating the relative biological response of male brown-banded cockroaches to the active fraction of a natural cockroach pheromone and a compound according to the present invention, as measured by electroantennograms.

The electrophysiological response of male brown-banded cockroaches to compound 14 prepared in Example 2 (hereafter "compound 14") and the active fraction of Example 1 were measured by performing electroantennograms according to the procedures described in Schal et al., *Site of pheromone production in female Supella longipalpa (f.) (Dictyoptera: Blattellidae): Behavioral, electrophysiological, and morphological evidence*, 85 Annals of the Entomological Society of America 605–611 (1992). The results are illustrated by FIG. 1. As shown by FIG. 1, male brown-banded cockroaches exhibit an electrophysiological response to both the active fraction and compound 14.

Example 4

The behavioral response of brown-banded cockroaches to the active fraction and compound 14 was evaluated according to the procedures described in Liang and Schal, *Effects of pheromone concentration and photoperiod on the behavioral response sequence to sex pheromone in the male brown-banded cockroach, Supella longipalpla*, 3 Journal of Insect Behavior 211–223 (1990). Male, brown-banded cockroaches were acclimated to a two-choice plexiglass straight tube (115 cm×4.5 cm internal diameter). At the end of one branch of the tube was a dispenser loaded with either active fraction or the inventive compound 5-(2,4-dimethylheptanyl)-3-methyl-2H-pyran-2-one (i.e., compound 14). At the end of the other branch was a control dispenser which was loaded only with hexane and no attractant. In the middle of the cockroachs' scotophase, the acclimated, male, brown-banded cockroaches were released downwind of the dispensers and allowed to choose between the control and either the active fraction or compound 14. Three sets of eight runs each were performed using active fraction versus the control and compound 14 versus the control. In the first set, the amount of active fraction or compound 14 used was 1 ng. In the second set, the amount of active fraction or compound 14 was 10 ng. In the third set, the amount of active fraction or compound 14 was 100 ng. In each run, the cockroaches chose the attractant-containing dispenser, regardless of whether the attractant was the active fraction or compound 14. None of the cockroaches chose the control dispenser. These results indicate that compound 14 is an effective attractant for cockroaches and, in fact, is as effective as the active fraction at levels of 1 ng and above.

Example 5

Figure 3:
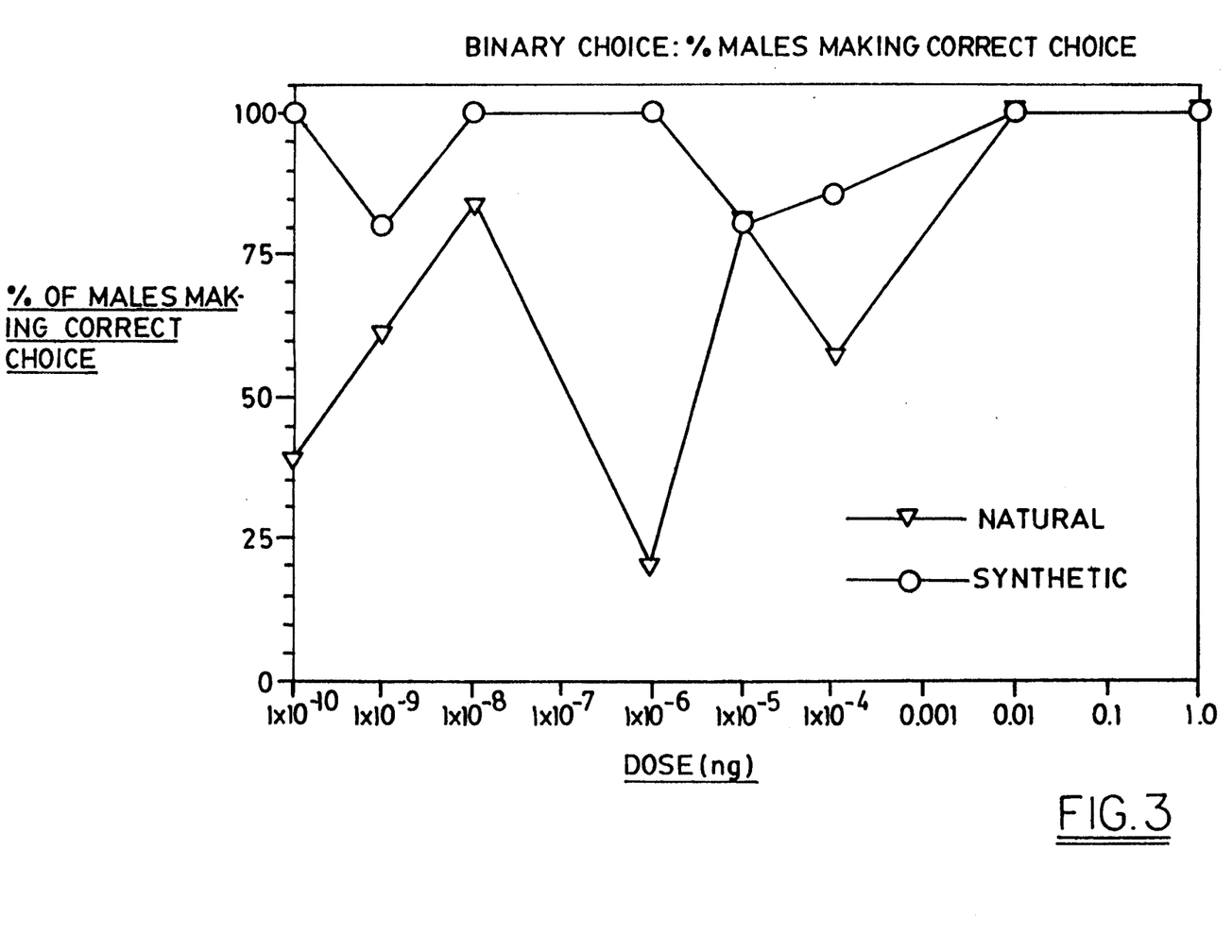
FIG. 3 is a graph illustrating the relative behavioral response of male brown-banded cockroaches to the active fraction of a natural cockroach pheromone and a compound according to the present invention, as measured by the relative percentages of cockroaches choosing an attractant-loaded dispenser over a control containing no attractant.
Figure 4:
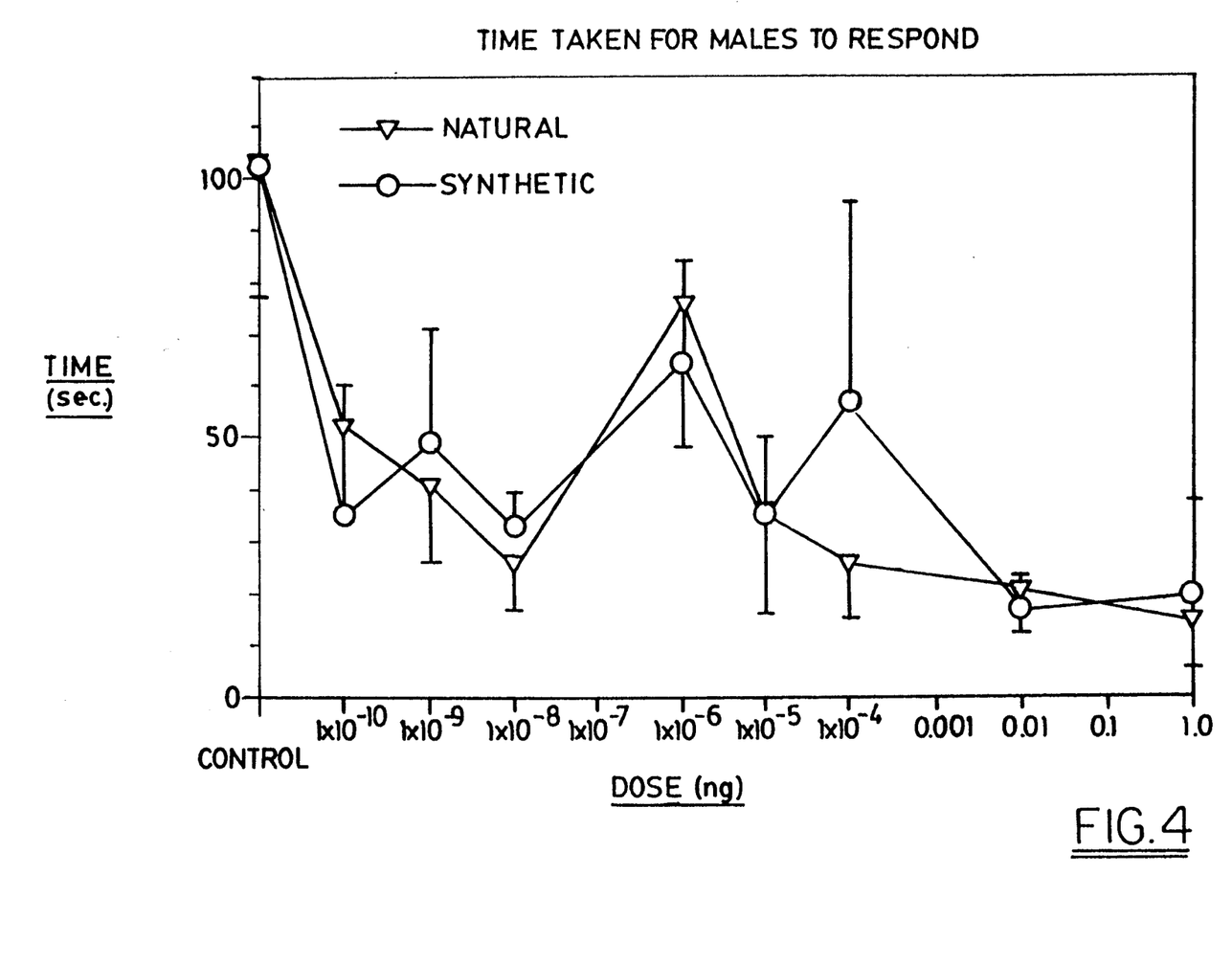
FIG. 4 is a graph illustrating the relative time required for male brown-banded cockroaches to respond to the active fraction of a natural cockroach pheromone and a compound according to the present invention.

The behavioral response of brown-banded cockroaches to active fraction and compound 14 was evaluated at levels of 1 ng and below according to the procedures described in Example 4 above. As above, the attractant-containing dispensers were loaded with either active fraction or compound 14. The dose of attractant ranged from 1 ng to $1 \times 10^{-10}$ ng. The experimental results are outlined in Table I and illustrated in FIGS. 2 through 4. "Dose" is the amount of active fraction or compound 14 used in nanograms ("ng"). "Natural Resp." represents the ratio of cockroaches which were attracted to either the dispenser containing active fraction or the dispenser containing only hexane versus the number of cockroaches tested. For example, "$\frac{7}{8}$" means that eight cockroaches were tested and seven were attracted to one of the two dispensers. "Synth. Response" represents the ratio of cockroaches which were attracted to either the dispenser containing compound 14 or the dispenser containing only hexane versus the number of cockroaches tested. "Right" represents the ratio of cockroaches which were attracted to the "right" dispenser (i.e., the dispenser containing either the active fraction or compound 14) versus the total number of cockroaches which were attracted to either of the dispensers (i.e., the cockroaches attracted to the "right" dispenser plus the cockroaches attracted to the dispenser containing only hexane). "Time" represents the average time it took the cockroach to respond in seconds, ± the standard deviation. The control data represents the number of cockroaches which responded when both dispensers contained only hexane.

cockroaches to the active fraction and compound 14 is comparable. As shown by FIG. 3, the number of cockroaches making the right choice after reaching the dispensers was generally high for both the active fraction and compound 14, indicating that compound 14 is an effective cockroach attractant. As shown by FIG. 4, the time required for the male cockroaches to respond generally increases as the dose of attractant decreases. However, the response time of the cockroaches to the active fraction and compound 14 is comparable, indicating that compound 14 is an effective cockroach attractant.

Example 6

The behavioral response of brown-banded cockroaches to compound 14 was evaluated by exposing male brown-banded cockroaches to two types of cockroach traps loaded with compound 14. Six "Raid TM Waterbug and Roach Traps", sold by S. C. Johnson & Son, Racine, Wis. were placed in an approximately 12 ft.×7 ft. walk-in chamber. Three traps were loaded with compound 14 (two with 100 ng, one with 1000 ng). Three traps contained no compound 14 and served as control traps. 100 male brown-banded cockroaches were then released into the chamber. The traps were checked after 24 hours and after four days to determine the number of cockroaches trapped. The results are shown in Table II below.

TABLE II

| TRAP # | Amt. (ng) | COCKROACHES | | |
|---|---|---|---|---|
| | | 24 hrs. | 4 days | TOTAL |
| 1 | 0 (control) | 4 | 2 | 6 |
| 2 | 0 (control) | 1 | 2 | 3 |
| 3 | 0 (control) | 3 | 3 | 6 |
| 4 | 100 | 12 | 6 | 18 |
| 5 | 100 | 10 | 8 | 18 |
| 6 | 1000 | 9 | 2 | 11 |

As shown by Table II, the traps loaded with compound 14 caught a total of 47 cockroaches, while the control traps caught a total of only 15 cockroaches. These results show that cockroach traps loaded with compound 14 are more effective than the unloaded traps, indicating that compound 14 is an effective cockroach attractant.

Example 7

The behavioral response of brown-banded cockroaches to compound 14 was evaluated in the manner described above, except that four Mr. Sticky TM roach traps, sold by Brody Enterprises, Fair Lawn, N.J., were used. Two of the traps were loaded with 10 ng of compound 14 and two traps contained no compound 14 and served as control traps. The traps were checked for the

TABLE I

| Dose (ng) | Natural Resp. | Right | Time (sec) | Synth. Resp. | Right | Time (sec) |
|---|---|---|---|---|---|---|
| 1.0 | 8/8 | 8/8 | 14.8 ± 8.5 | 8/8 | 8/8 | 19.5 ± 18.9 |
| $1 \times 10^{-2}$ | 5/5 | 5/5 | 19.0 ± 6.3 | 6/6 | 5/5 | 16.8 ± 5.5 |
| $1 \times 10^{-4}$ | 7/8 | 4/7 | 25.4 ± 9.9 | 7/8 | 6/7 | 57.1 ± 38.4 |
| $1 \times 10^{-5}$ | 5/7 | 4/5 | 35.6 ± 19.4 | 5/6 | 4/5 | 35.2 ± 15.1 |
| $1 \times 10^{-6}$ | 5/8 | 1/5 | 75.8 ± 27.5 | 4/7 | 4/4 | 64.5 ± 20.2 |
| $1 \times 10^{-8}$ | 6/7 | 5/6 | 25.4 ± 8.9 | 5/8 | 6/5 | 32.8 ± 6.6 |
| $1 \times 10^{-9}$ | 5/8 | 3/5 | 40.0 ± 14.1 | 5/7 | 4/5 | 49.0 ± 22.1 |
| $1 \times 10^{-10}$ | 8/8 | 3/8 | 51.9 ± 16.4 | 5/7 | 5/5 | 35.2 ± 25.6 |
| control | 3/8 | 0/3 | 102.3 ± 24.8 | | | |

Figure 2:
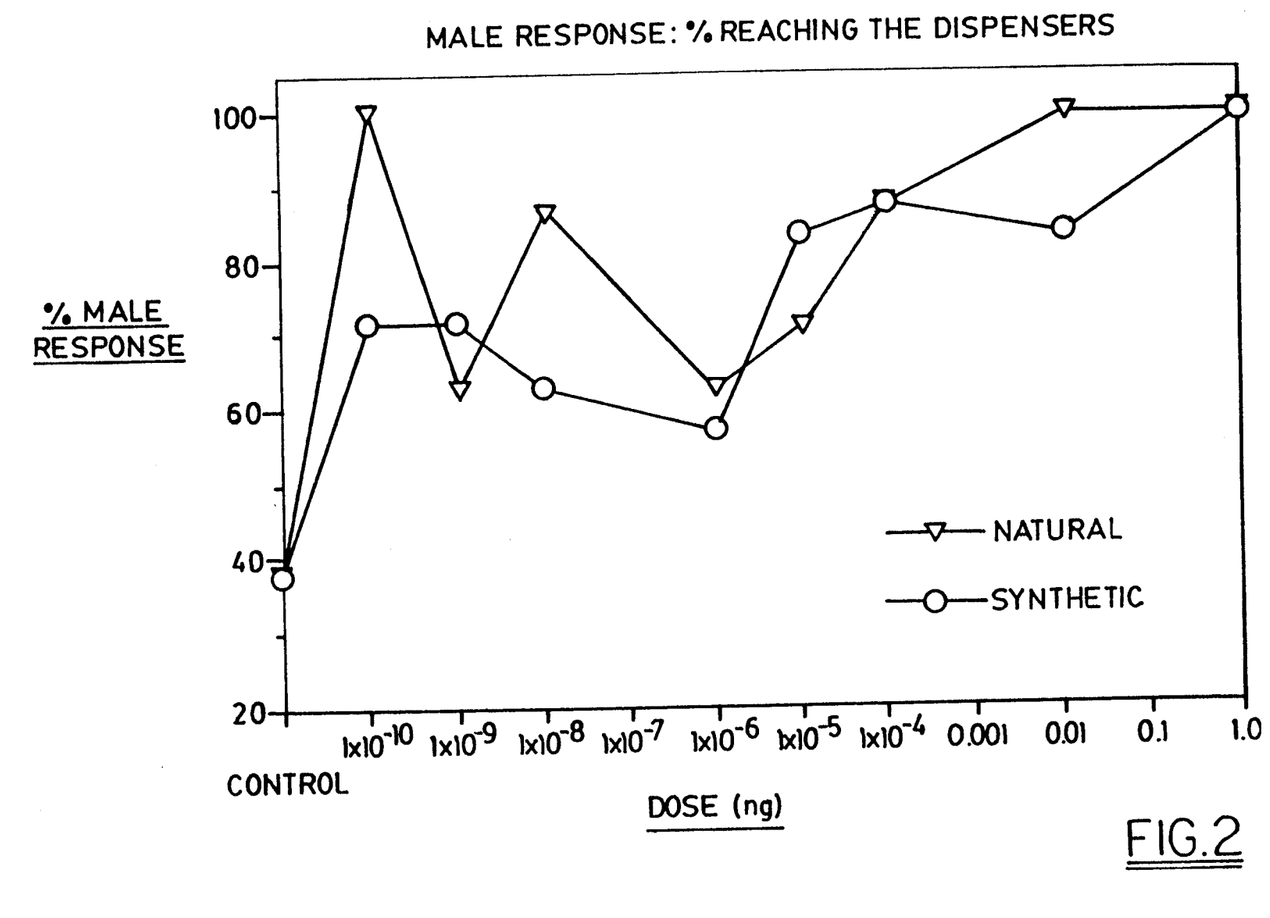
FIG. 2 is a graph illustrating the relative behavioral response of male brown-banded cockroaches to the active fraction of a natural cockroach pheromone and a compound according to the present invention, as measured by the percentage of cockroaches attracted to two dispensers, one containing attractant and one containing no attractant.

As shown by FIG. 2, the percentage of cockroaches actually reaching the dispensers decreases as the dose of attractant decreases. However, the response of the number of cockroaches caught after 24 hours. The results are shown in Table III below.

TABLE III

| TRAP # | Amt. (ng) | COCKROACHES 24 hrs. |
|---|---|---|
| 1 | 0 (control) | 1 |
| 2 | 0 (control) | 0 |
| 3 | 10 | 14 |
| 4 | 10 | 9 |

As shown by Table III, the traps loaded with compound 14 caught a total of 23 cockroaches, while the control traps caught only 1 cockroach. Therefore, cockroach traps are more effective when loaded with compound 14 than the trap alone, indicating that compound 14 is an effective cockroach attractant.

Although the invention has been described in detail for the purpose of illustration, it is understood that such detail is solely for that purpose, and variations can be made therein by those skilled in the art without departing from the spirit and scope of the invention which is defined by the following claims.

What is claimed is:
1. A pyran having the formula:

wherein:
$R^1$ is an H, methyl, ethyl, propyl, or methoxy group and
$R^2$ is a branched alkyl side chain having from 7 to 11 carbons.

2. A pyran according to claim 1, wherein $R^2$ is a 2,4-dimethyl-substituted alkyl group.

3. A pyran according to claim 2, wherein $R^1$ is methyl and $R^2$ is 2,4-dimethylheptanyl.

4. An attractant blend comprising two or more stereoisomers of a compound having the formula:

wherein:
$R^1$ is an H, methyl, ethyl, propyl, or methoxy group,
$R^2$ is a branched alkyl side chain having from 7 to 11 carbons.

5. An attractant blend according to claim 4, wherein $R^2$ is a 2,4-dimethyl-substituted alkyl group.

6. An attractant blend according to claim 4, wherein $R^1$ is methyl and $R^2$ is 2,4-dimethylheptanyl.

7. An attractant blend according to claim 6, wherein said blend includes four stereoisomers of said compound.

8. An attractant blend according to claim 7, wherein said blend of stereoisomers is racemic.

9. A method of attracting cockroaches comprising exposing said cockroaches to a trap charged with between about $1 \times 10^{-4}$ to 100 μg of an attractant having the formula:

wherein:
$R^1$ is an H, methyl, ethyl, propyl, or methoxy group and
$R^2$ is a branched alkyl side chain having from 7 to 11 carbons.

10. A method according to claim 9, wherein $R^1$ is a 2, 4-dimethyl-substituted alkyl group.

11. A method according to claim 9, wherein $R^1$ is methyl and $R^2$ is 2,4-dimethylheptanyl.

12. An enol lactone having the formula:

wherein:
$R^1$ is an H, methyl, ethyl, propyl, or methoxy group and
$R^2$ is a branched alkyl side chain having from 7 to 11 carbons.

13. An enol lactone according to claim 12 wherein $R^2$ is a 2,4-dimethyl-substituted alkyl group.

14. A enol lactone according to claim 12, wherein $R^1$ is methyl and $R^2$ is 2,4-dimethylheptanyl.

15. A method of disrupting cockroach mating, comprising the step of exposing a cockroach population to a pyran having the formula:

wherein:
$R^1$ is an H, methyl, ethyl, propyl, or methoxy group and
$R^2$ is a branched alkyl side chain having from 7 to 11 carbons, in a quantity sufficient to disrupt mating.

* * * * *